(12) United States Patent
Raheem et al.

(10) Patent No.: US 7,884,121 B2
(45) Date of Patent: Feb. 8, 2011

(54) PROCESS FOR THE PREPARATION OF PHENYLCARBAMATES

(75) Inventors: Mohammed Abdul Raheem, Brantford (CA); Zhi-Xian Wang, Brantford (CA); Eckardt C. G. Wolf, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 839 days.

(21) Appl. No.: 11/808,430

(22) Filed: Jun. 11, 2007

(65) Prior Publication Data

US 2008/0306280 A1 Dec. 11, 2008

(51) Int. Cl.
A61K 31/4172 (2006.01)
C07D 233/64 (2006.01)
(52) U.S. Cl. .................................. 514/399; 548/341.5
(58) Field of Classification Search .............. 548/341.5; 514/399
See application file for complete search history.

(56) References Cited

U.S. PATENT DOCUMENTS

| 4,948,807 A | 8/1990 | Rosin |
| 5,602,176 A | 2/1997 | Enz |

FOREIGN PATENT DOCUMENTS

| CA | 1284501 | 5/1991 |
| CN | 1486973 | 4/2004 |
| EP | 0193926 | 7/1990 |
| GB | 2409453 | 6/2005 |
| WO | WO 03/101917 A2 | 12/2003 |
| WO | WO 03/101917 A3 | 12/2003 |
| WO | WO 2004/037771 | 5/2004 |
| WO | WO 2005/058804 A1 | 6/2005 |
| WO | WO 2005/061446 A2 | 7/2005 |
| WO | WO 2005/061446 A3 | 7/2005 |
| WO | WO 2007/014973 A2 | 2/2007 |
| WO | WO 2007/014973 A3 | 2/2007 |
| WO | WO 2007/026373 A2 | 3/2007 |
| WO | WO-2007/026373 A2 * | 3/2007 |
| WO | WO 2007/026373 A3 | 3/2007 |
| WO | WO 2007/025481 A1 | 8/2007 |

OTHER PUBLICATIONS

Amstutz, R. et al.; Cyclische phenyl-carbamate de Miotin-Typs and ihre Wirkung auf die acetylcholinesterase.; Helv. Chim. Acta; 1990; 73: 739-753.
Boezio, AA, et al.; Asymmetric, Catalytic Synthesis of alpha-Chiral Amines Using a Novel Bis(phosphine) Monoxide Chiral Ligand.; J. Am. Chem. Soc.; 2003; 125: 14260-14261.
J. of East China Normal University (Natural Science), 2001: 61-65.
Grzyb, J.A. et al.; Carbamoylimidazolium and thiocarbamoylimidazolium salts: novel reagents . . . amides.; Tetrahedron; 2005; 61:7153-7175.

Chen C-P; et al.; A general enantioselective synthesis of alpha-arylethylamines.; Tetrahedron Letters; 1991; 32: 7175-7178.

* cited by examiner

Primary Examiner—Susannah Chung
Assistant Examiner—Janet L Coppins

(57) ABSTRACT

This invention relates to a process for the preparation of an aminoalkyl phenyl carbamate compound of formula 1,

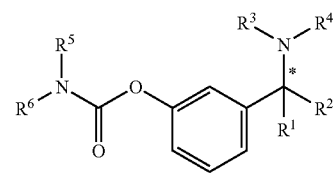

wherein $R^1$ and $R^2$ independently are hydrogen or $C_{1-6}$ alkyl; $R^3$ and $R^4$ are the same or different and each is a lower alkyl; or $R^3$ and $R^4$ together with the nitrogen to which they are attached form a cyclic moiety of a three to eight-member ring, with or without a hetero atom like nitrogen or oxygen; $R^5$ and $R^6$ independently are hydrogen, linear, branched or cyclic $C_{1-6}$ alkyl, allyl, propargyl or benzyl; or $R^5$ and $R^6$ together with the nitrogen to which they are attached form a cyclic moiety of three to eight member ring, with or without a hetero atom like nitrogen or oxygen; the carbon center marked with "*" is racemic or enantiomerically enriched (R)- or (S)-configuration; and pharmaceutically acceptable addition salts, and crystalline and amorphous forms thereof comprising the steps of:

i) converting an amine $R^5R^6NH$ to a carbamoylimidazolium salt of formula 3

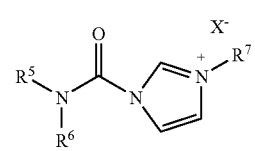

wherein $R^5$ and $R^6$ are as defined above; $X^-$ is a counterion and $R^7$ is an alkyl or aryl group;

ii) reacting in a solvent at a controlled reaction temperature the compound of formula 3 with a compound of formula 4,

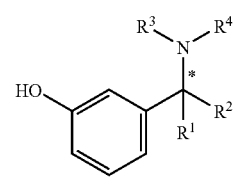

wherein $R^1$, $R^2$, $R^3$, $R^4$ and "*" are as defined above to give the compound of formula 1; and
iii) isolating the compound of formula 1.

36 Claims, 3 Drawing Sheets

Figure 1. PXRD of crystalline form of Rivastigmine hydrogen Tartrate
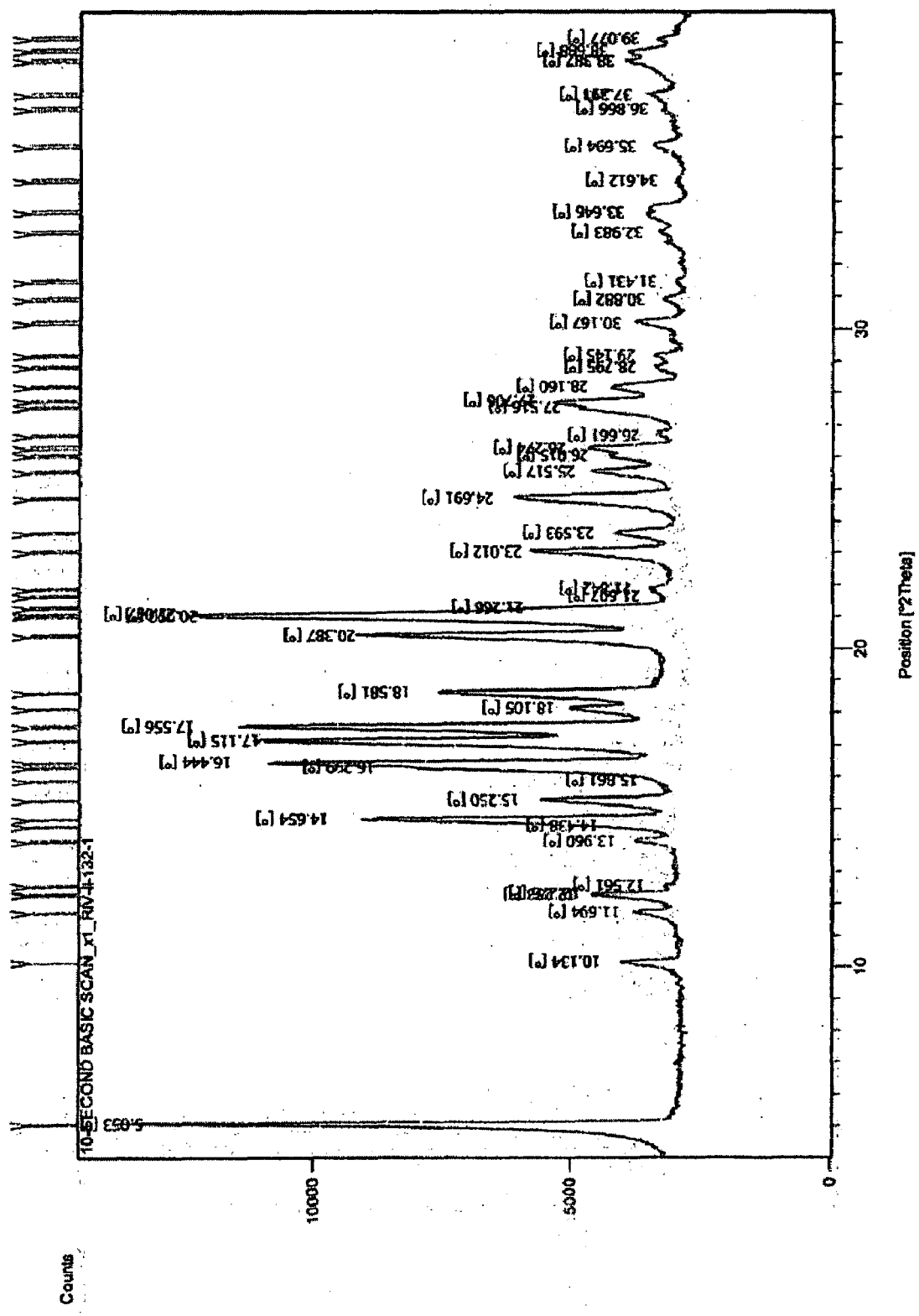

Figure 2. PXRD of amorphous form of Rivastigmine hydrogen Tartrate.
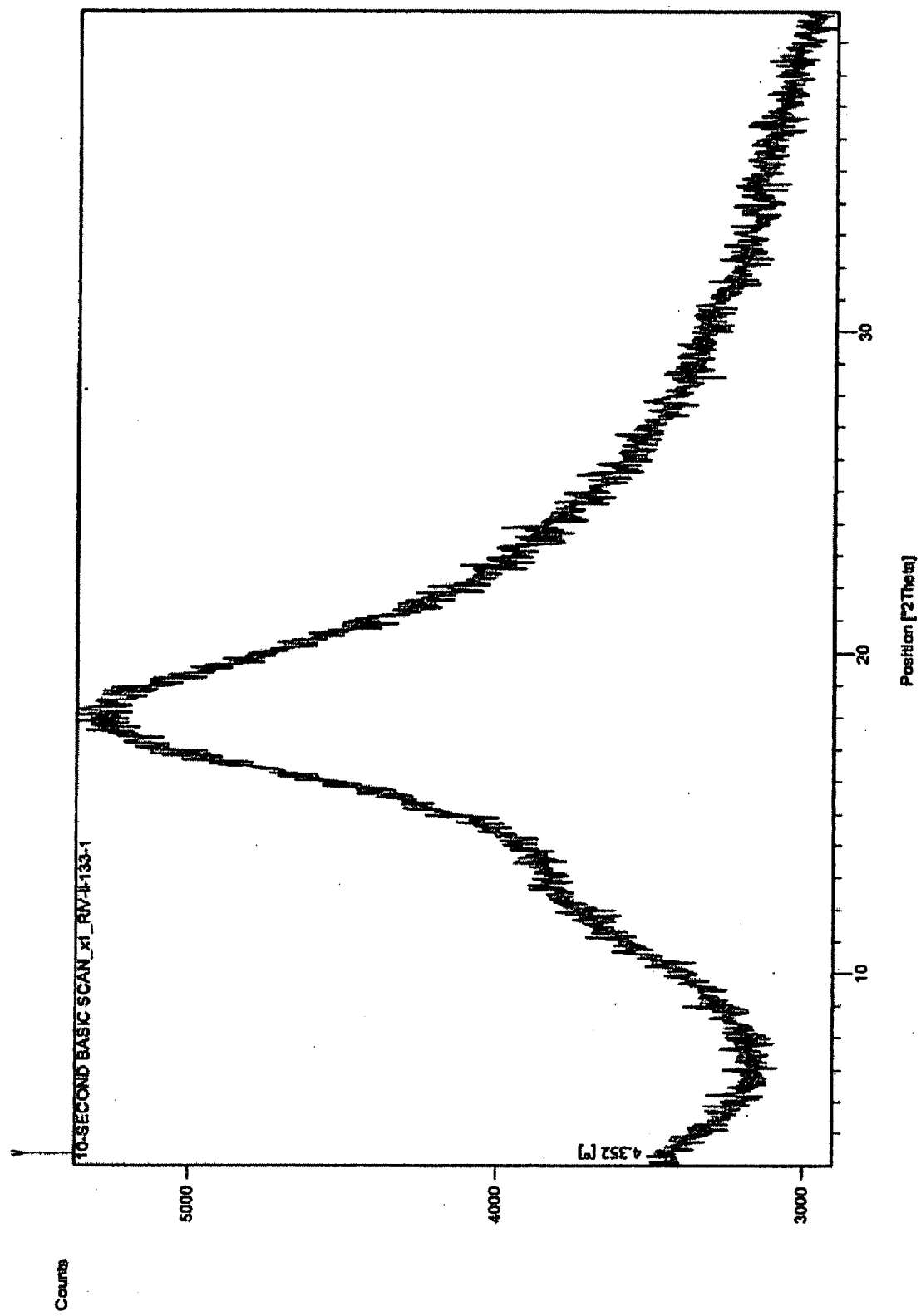

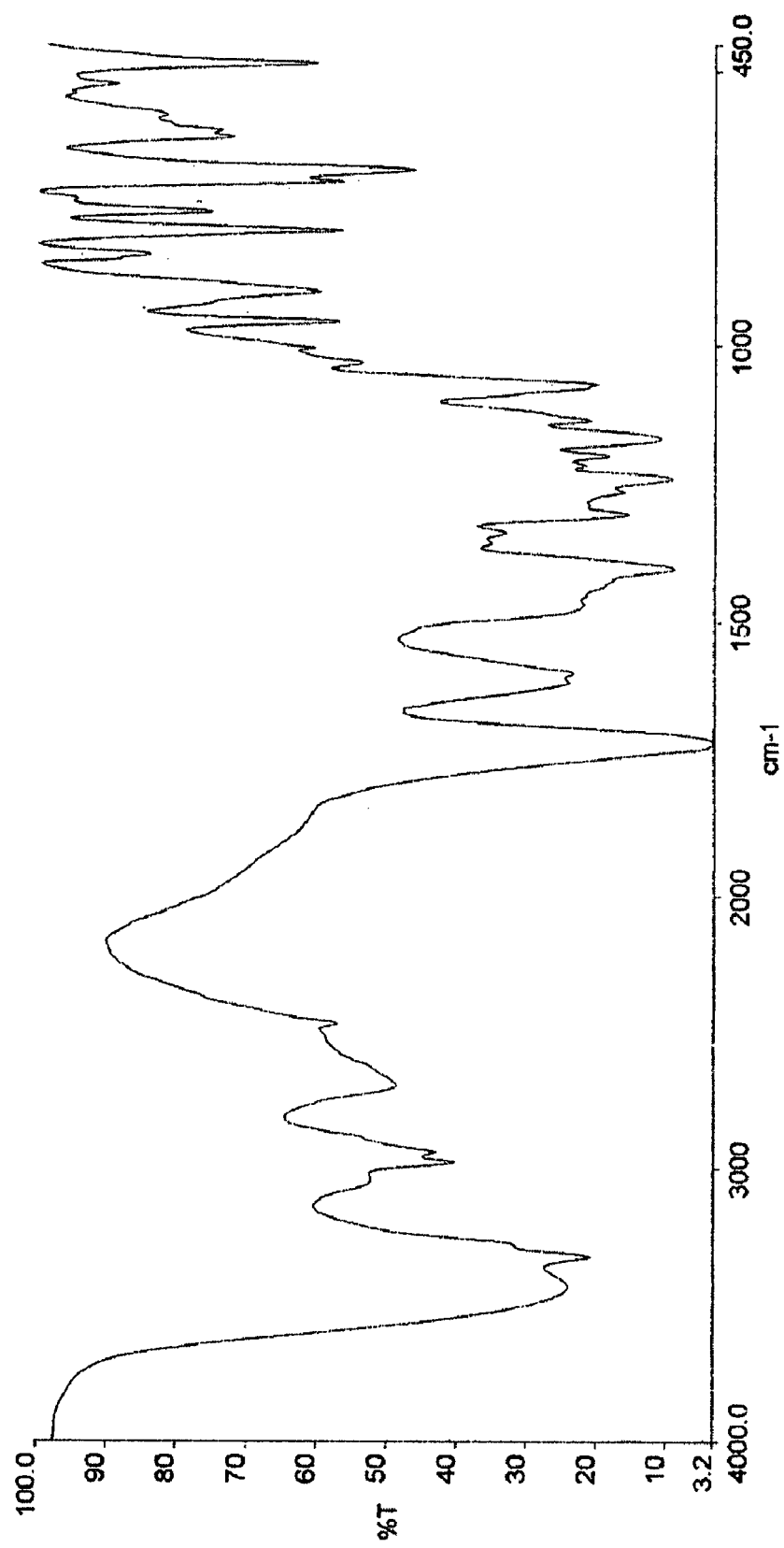
Figure 3. IR of amorphous form of Rivastigmine hydrogen Tartrate.

PROCESS FOR THE PREPARATION OF PHENYLCARBAMATES

FIELD OF THE INVENTION

The present invention relates to a process for the preparation of aminoalkyl phenyl carbamates of formula 1,

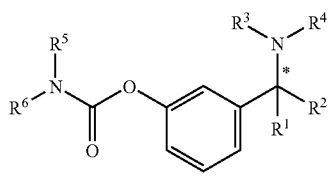

wherein $R^1$ and $R^2$ independently are hydrogen or lower alkyl; $R^3$ and $R^4$ are the same or different and each is a lower alkyl; or $R^3$ and $R^4$ together with the nitrogen to which they are attached form a cyclic moiety of a three to eight-member ring, with or without a hetero atom like nitrogen or oxygen; $R^5$ and $R^6$ independently are hydrogen, linear, branched or cyclic C1-C6 alkyl, allyl, propargyl or benzyl; or $R^5$ and $R^6$ together with the nitrogen to which they are attached form a cyclic moiety of three to eight member ring, with or without a hetero atom like nitrogen or oxygen; the carbon center marked with "*" can be racemic or enantiomerically enriched (R)- or (S)-configuration.

According to an aspect of the invention, the process of the present invention relates to the preparation of racemic and enantiomerically enriched forms of ethylmethylcarbamic acid 3-[1-(dimethylamino)ethyl]phenyl ester, commonly known as Rivastigmine.

BACKGROUND OF THE INVENTION

Certain aminoalkyl phenylcarbamates are selective acetylcholine esterase inhibitors and are therefore potentially useful as pharmaceuticals for the treatment of brain disorders such as dementia, Alzheimer's Disease, Huntington's Chorea, tardive dyskinesias, confusion disorders and ataxia. One such compound, the (2R,3R)-hydrogen tartrate salt of (S)-ethylmethylcarbamic acid 3-[1-(dimethylamino)ethyl]phenyl ester (Rivastigmine hydrogen tartrate, 2), is marketed as a pharmaceutical for the treatment of dementia of the Alzheimer's type.

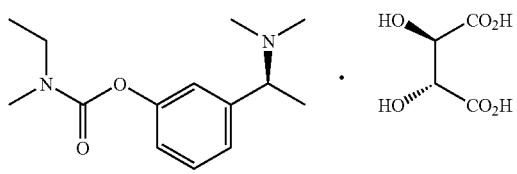

Rivastigmine hydrogen tartrate,

Processes for the preparation of these types of aminoalkyl phenylcarbamates are described in patents U.S. Pat. No. 4,948,807, EP 193926, U.S. Pat. No. 5,602,176, GB 2409453, CN 1486973, WO 2004/037771, WO 2007/026373, WO 2007/025481 and WO 2007/014973. The patents disclose the preparation of phenyl carbamate compounds involving reaction of phenol compounds with appropriate isocyanates or carbamoyl halides. The process using isocyanates involves the use of benzene as a solvent. Isocyanates such as lower alkyl isocyanates are hazardous to handle due to their toxic and volatile nature.

The other reported alternative is the use of carbamoyl halides along with reactive bases like sodium hydride, to prepare the carbamates. The carbamoyl halides are carcinogenic substances and are not easy to handle on industrial scale. In addition, the use of a reactive base like sodium hydride on an industrial scale is hazardous and operationally non-user friendly due to its pyrophoric and reactive nature.

PCT application WO 03/101917 discloses a process for the preparation of the title phenyl carbamate compounds involving reaction of phenol compounds with an alkylamine-4-nitrophenyl carbamate. The invention partially overcomes the deficiency posted by the use of isocyanates or carbamoyl halides reported in the prior art. However, the reaction requires harsh conditions and long reaction time. For example, in Example 3 of the application, the reaction of 3-(1-dimethylaminoethyl)phenol and N-ethyl-N-methyl-4-nitrophenyl carbamate was carried out in dimethylsulfoxide (DMSO) in the presence of anhydrous potassium carbonate at 90-100° C. for 35-40 hours. In addition, the reaction condition may not be suitable for the reaction of chiral intermediate such as (S)-3-(1-dimethylaminoethyl)phenol since the stereochemistry at the chiral center may be racemized when heated with a base for an extended period of time.

Crystalline forms of Rivastigmine hydrogen tartrate have been disclosed in the prior art, for example, U.S. Pat. No. 5,602,176 and WO 2007/026373. The characteristics affected by polymorphism include solubility, dissolution rate, stability, hygroscopicity and solid-state reactivity. The effect of polymorphism on bioavailability is the most important consequence if the bioavailability is mediated via dissolution. The amorphous form of Rivastigmine hydrogen tartrate has not been reported.

It is therefore an object of the invention to provide a more industrially applicable process for the preparation of aminoalkyl phenyl carbamate compounds.

It is a further object of the invention to use less toxic substances in the formation of racemic and enantiomerically-enriched (R)- or (S)-Rivastigmine, and their pharmaceutically-acceptable addition salts.

It is yet a further object of the invention to provide an amorphous form of Rivastigmine such as Rivastigmine hydrogen tartrate.

Further and other objects of the invention will become apparent to those skilled in the art when considering the following summary of the invention and the more detailed description of the embodiments of the invention described herein.

SUMMARY AND DETAILED DESCRIPTION OF THE INVENTION

According to one aspect of the invention, a process is provided for the preparation of an aminoalkyl phenyl carbamate compound of formula 1,

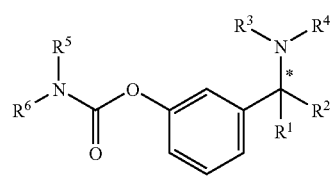

wherein $R^1$ and $R^2$ independently are hydrogen or $C_{1-6}$ alkyl; $R^3$ and $R^4$ are the same or different and each is a $C_{1-6}$ alkyl; or $R^3$ and $R^4$ together with the nitrogen to which they are attached form a cyclic moiety of a three to eight-member ring, with or without a hetero atom like nitrogen or oxygen; $R^5$ and $R^6$ independently are hydrogen, linear, branched or cyclic $C_{1-6}$ alkyl, allyl, propargyl or benzyl; or $R^5$ and $R^6$ together with the nitrogen to which they are attached form a cyclic moiety of three to eight member ring, with or without a hetero atom like nitrogen or oxygen; the carbon center marked with "*" can be racemic or enantiomerically enriched (R)- or (S)-configuration; and pharmaceutically acceptable addition salts thereof, the process comprising the steps of:

i) converting an amine $R^5R^6NH$ to carbamoylimidazolium salt of formula 3

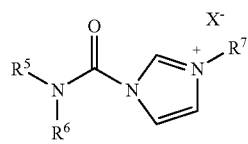

3 wherein $R^5$ and $R^6$ are as defined above; $X^-$ is a counterion and $R^7$ is an alkyl or aryl group;

ii) reacting in a solvent at a controlled reaction temperature, the compound of formula 3 with a compound of formula 4,

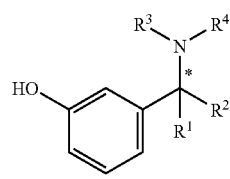

4 wherein $R^1$, $R^2$, $R^3$, $R^4$ and "*" are as defined above to form the compound of formula 1; and iii) isolating the compound of formula 1.

The aminoalkyl phenyl carbamates described herein may form pharmaceutically acceptable acid salts with a wide variety of pharmaceutically acceptable organic and inorganic acids.

Surprisingly, we have discovered that the compound of formula 4 can react with a carbamoylimidazolium salt of formula 3 to produce the compound of formula 1 with very good yield and high purity. In other words, the stereochemical integrity of the chiral center is maintained. Moreover, the process avoids using carcinogenic substances such as carbamoyl halides and highly toxic reagents such as isocyanates. For these reason, this method is advantageously useful for the preparation of optically enriched aminoalkyl phenyl carbamates such as (S)-Rivastigmine.

The compounds of formula 4 and their optically pure enantiomers can be obtained using the methods previously described in the art, for example, the methods disclosed in U.S. Pat. No. 4,948,807, EP 193926, CA 1284501, U.S. Pat. No. 5,602,176, WO 2003/101917, WO 2004/037771, CN 1486973, WO 2007/025481, *Helv. Chim. Acta*, 1990, 73, 739-753, *J. Amer. Chem. Soc.* 2003, 125, 14260-14261, and *Journal of East China Normal University* (*Natural Science*), 2001, 61-65. The compound of formula 4 can be used as free-base or acid addition salt form, for example, hydrochloride salt, hydrobromide salt, oxalate, and camphorsulfonic acid salt, or base addition salt form such as sodium salt, potassium salt and lithium salt.

According to another aspect of the present invention, the counterion in compound 3 may be selected from iodide ($I^-$), bromide ($Br^-$), chloride ($Cl^-$), fluoride ($F^-$), methylsulfate [$(MeO)SO_3^-$], sulfate ($SO_4^{2-}$), tetrafluoroborate ($BF_4^-$) and trifluoromethylsulfonate ($OTf^-$), and the preferable counterion is $I^-$, $Br^-$, $(MeO)SO_3^-$, $BF_4^-$ and $OTf^-$. $R^7$ may be an alkyl or aryl group, and the preferable alkyl groups are $C_1$-$C_7$ alkyl groups such as methyl, ethyl, propyl and butyl.

The compound of formula 3 can be prepared from an amine $R^5R^6NH$ by converting it to an imidazole-1-carboxamide intermediate, for example, by reacting the amine $R^5R^6NH$ with N,N'-carbonyldiimidazole (CDI), and followed by reacting with $R^7X$ (Route A), wherein $R^7$ and X are defined as above.

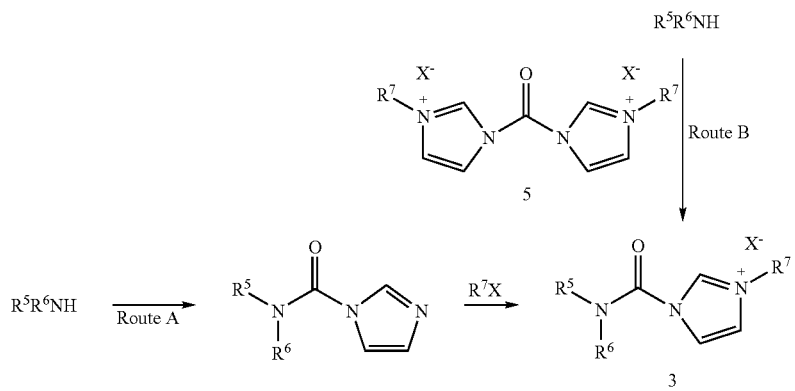

The compound of formula 3 can be also prepared from an amine $R^5R^6NH$ by reacting the amine with the 1,1'-carbonylbis(3-alkylimidazolium) salt of formula 5 (Route B), wherein $R^7$ and X are as defined above.

The compound of formula 3 may be isolated from the reaction mixture and used for the next step, or can be used directly without isolation. The one-pot approach is preferred because it employs less solvent, requires reduced production time and the yield is higher.

The reaction of compound 3 with compound 4 may be carried out in the same solvent as the previous step, or a different solvent selected from chlorinated hydrocarbons such as dichloromethane, dichloroethane and chlorobenzene; alkyl and aryl nitriles such as acetonitrile; alkyl carboxylic acid esters such as ethyl acetate and methyl acetate; cyclic or acyclic ethers such as 1,2-dimethoxyethane, dimethoxymethane, tetrahydrofuran and 1,4-dioxane; alkyl cyclic and acyclic amides such as N,N-dimethylformamide, N,N-dimethylacetamide and 1-methyl-2-pyrrolidinone; cyclic or acyclic alkyl sulfoxides and sulfones such as dimethylsulfoxide and tetramethylene sulfone; and aromatics such as toluene and xylenes. The preferred solvents are dichloromethane, acetonitrile, tetrahydrofuran, ethyl acetate and methyl acetate. Where the expression "controlled reaction temperature" is used herein, it is meant to indicate a temperature range from about −10° C. to about 150° C. and preferably from about 20° C. to about 100° C.

When the acid addition salt form of compound 4 is used, the reaction may be carried out in the presence of a base or a mixture of bases. The suitable bases include inorganic and organic bases, such as potassium carbonate, sodium carbonate, lithium carbonate, sodium hydride, triethylamine, diisopropylethylamine, pyridine and mixtures thereof.

The processes of the instant invention may also be used for preparing both enantiomerically enriched (R)- and (S)-stereoisomers and racemic mixtures of aminoalkyl phenyl carbamates of formula 1. It is understood by the skilled person that the specific enantiomerically enriched stereoisomers may be obtained by resolution of the racemic product, intermediates, or in some cases the starting materials. Thus, when a racemic mixture of aminoalkyl phenyl carbamates 1 is produced using the present processes, the product can be resolved into its specific isomers, namely, the (R)- or (S)-stereoisomer.

Further, according to another aspect of the invention there is provided a process for the preparation of racemic and enantiomerically enriched forms of ethylmethylcarbamic acid 3-[1-(dimethylamino)ethyl]phenyl ester of formula 6

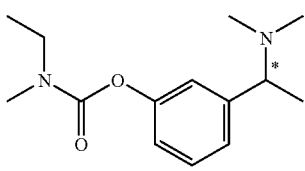

6 wherein the carbon centre designated "*" can be racemic or enantiomerically enriched in the (R)- or (S)-configuration, comprising the steps of:

i) converting an amine N-ethyl-N-methylamine to carbamoylimidazolium salt of formula 7

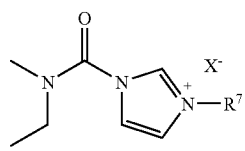

7 wherein X⁻ is a counterion and R⁷ is an alkyl or aryl group;

ii) reacting in a solvent at a controlled reaction temperature the compound of formula 7 with a compound of formula 8,

8 wherein the carbon centre designated "*" is as defined above, to form the compound of formula 6; and iii) isolating the compound of formula 6.

The detailed reaction conditions and definitions are the same as disclosed previously.

The compound of formula 6 described herein can form pharmaceutically acceptable acid addition salts with a wide variety of organic and inorganic acids. Of particular utility is the compound of formula 6 having the (S)-configuration and forming a salt with (2R,3R)-hydrogen tartaric acid. The resulting product is (S)-ethylmethylcarbamic acid 3-[1-(dimethylamino)ethyl]phenyl ester (2R,3R)-hydrogen tartrate, commonly known as Rivastigmine hydrogen tartrate.

In yet another embodiment of the invention there is provided an amorphous form of Rivastigmine such as amorphous Rivastigmine hydrogen tartrate. The product produced by the present invention can be in a crystalline form or an amorphous form and can be produced by treating the compound of formula 6 with (2R,3S)-hydrogen tartaric acid in a recrystallizing solvent such as, for example, water or isopropanol. Amorphous Rivastigmine hydrogen tartrate is the preferable form due to its greater solubility and dissolution rate compared to crystalline Rivastigmine hydrogen tartrate.

BRIEF DESCRIPTION OF THE DRAWINGS

FIG. 1 is a Powder X-Ray Diffraction (PXRD) pattern of the crystalline form of rivastigmine hydrogen tartrate prepared according to the process of the invention FIG. 2 is a Powder X-Ray Diffraction (PXRD) pattern of the amorphous form of rivastigmine hydrogen tartrate prepared according to the process of the invention.

FIG. 3 is an Infra-Red (IR) spectrum of the amorphous form of rivastigmine hydrogen tartrate prepared according to the process of the invention.

The following non-limiting examples further illustrate the manner of carrying out the inventive process described herein.

EXAMPLE 1

Preparation of N-ethyl-N-methyl-1H-imidazole-1-carboxamide

To the cooled (ice-water bath) suspension of 1,1'-carbonyldiimidazole (178.4 g, 1.10 moles) in dichloromethane (720 mL) was added N-ethylmethylamine (59.1 g, 1 mole) keeping the internal temperature below 10° C. during addition. The reaction mixture was stirred at 20-25° C. for 2-3 hours and then cooled to 0-5° C. The reaction mixture was quenched by slow addition of water (720 mL) keeping the IT<10° C. The aqueous and organic phases were separated and the aqueous phase was extracted with dichloromethane. The combined organic extracts were washed with water. The organic phase was concentrated to give N-ethyl-N-methyl-1H-imidazole-1-carboxamide (138 g). $^1$H NMR (CDCl$_3$) δ7.90 (s, 1H); 7.24 (s, 1H); 7.08 (s, 1H); 3.47 (q, J=7.2 Hz, 2H); 3.07 (s, 3H); 1.27 (t, J=7.2 Hz, 3H).

EXAMPLE 2

Preparation of 1-[(N-ethyl-methylamino)carbonyl]-3-methyl-1H-midazolium iodide To the cooled solution of N-ethyl-N-methyl-1H-imidazole-1-carboxamide (22.2 g, 145.25 mmol) in acetonitrile (40 mL) was charged slowly with methyl iodide (22.3 g, 157.4 mmol) while keeping internal temperature below 10° C. The reaction mixture was stirred at 20-25° C. for 2-3 hours and then it was evaporated under vacuum to yield 1-[[N-ethyl-(N-methyl)amino]carbonyl]-3-methyl-1H-imidazolium iodide. $^1$H NMR (CDCl$_3$) δ 10.23 (s, 1H); 7.75 (s, 1H); 7.66 (s, 1H); 4.29 (s, 3H); 3.59 (q, J=7.2 Hz, 2H), 3.30 (s, 3H), 1.32 (t, J=7.2 Hz, 3H).

EXAMPLE 3

Preparation of 1-[(N-ethyl-methylamino)carbonyl]-3-methyl-1H-midazolium methyl sulfate To the cooled solution of N-ethyl-N-methyl-1H-imidazole-1-carboxamide (5 g, 32.7 mmol) in acetonitrile (10 mL) was added slowly dimethyl sulfate (4.12 g, 32.7 mmol). The reaction mixture was stirred at room temperature overnight and then was evaporated under vacuum to yield 1-[[N-ethyl-(N-methyl)amino]carbonyl]-3-methyl-1H-imidazolium methyl sulfate (9.1 g). $^1$H NMR (CDCl$_3$) δ 9.7 (s, 1H); 7.7 (s, 1H); 7.6 (s, 1H); 4.1 (s, 3H); 3.65 (s, 3H), 3.5 (q, J=7.2 Hz, 2H), 3.15 (s, 3H), 1.3 (t, J=7.2 Hz, 3H).

EXAMPLE 4

Preparation of (S)—N-Ethyl-N-methyl-3-[1-(dimethylamino)ethyl]-phenyl carbamate from (S)-3-[1-(Dimethylamino)ethyl]phenol and 1-[(N-ethyl-methylamino)carbonyl]-3-methyl-1H-imidazolium iodide Triethylamine (14.7 g, 145.2 mmol) and 1-[[N-ethyl-(N-methyl)amino]carbonyl}-3-methyl-1H-imidazolium iodide (42.9 g, 145.25 mmol) were added slowly to the cooled solution of (S)-3-[1-(dimethylamino)ethyl]phenol (20 g, 121.0 mmol) in acetonitirile (60 mL). The reaction mixture was stirred at 75-80° C. until reaction completion as determined by $^1$H NMR. The reaction mixture was evaporated and the obtained residue was diluted with water (40 mL) and toluene (60 mL) and then basified with 50% aq. NaOH solution at <10° C. The phases were separated and the aqueous phase was extracted with toluene. The combined organic phases were washed with water. The organic solution was evaporated under vacuum to give (S)—N-ethyl-N-methyl-3-[1-(dimethylamino)ethyl]phenyl carbamate (Rivastigmine free base). $^1$HNMR (CDCl$_3$) δ 7.29 (t, J=7.80 Hz, 1H); 7.13-6.90 (m, 3H); 3.50-3.35 (m, 2H); 3.24 (q, J=6.7 Hz, 1H); 3.02 (ad, 3H); 2.20 (s, 6H); 1.36 (d, J=6.7 Hz, 3H); 1.26-1.15 (m, 3H).

EXAMPLE 5

Preparation of (S)—N-Ethyl-N-methyl-3-[1-(dimethylamino)ethyl]-phenyl carbamate from (S)-3-[1-(Dimethylamino)ethyl]phenol (1S)-10-Camphorsulfonate Triethylamine (12.7 g, 125.8 mmol) was added slowly to a solution of (S)-3-[1-(dimethylamino)ethyl]phenol (1S)-10-camphorsulfonate (20 g, 50.3 mmol) in acetonitirile (60 mL) while keeping the internal temperature below 10° C. The reaction mixture was stirred for 0.5-1 hour. A solution of 1-[[N-ethyl-(N-methyl)amino]carbonyl]-3-methyl-1H-imidazolium iodide (14.3 g, 55.3 mmol) was then added slowly while keeping the internal temperature below 10° C. The reaction mixture was warmed to 75-80° C. and maintained until reaction completion as determined by $^1$H NMR. The reaction mixture was evaporated and the obtained residue was diluted with water (40 mL) and toluene (60 mL) and subsequently basified with 50% aq NaOH solution at internal temperature below 10° C. The phases were separated and the aqueous phase was extracted with toluene. The combined organic phases were washed with water. The organic solution was evaporated under vacuum to give (S)—N-ethyl-N-methyl-3-[1-(dimethylamino)ethyl]-phenyl carbamate (Rivastigmine free base) (12.5 g). The $^1$H NMR spectrum of the product was identical to that of example 4.

EXAMPLE 6

Preparation of crystalline form of (S)—N-Ethyl-N-methyl-3-[1-(dimethylamino)ethyl]-phenyl carbamate (2R,3R)-hydrogen tartrate (2R,3R)-Tartaric acid (9.0 g, 60.0 mmol) was added to a solution of (S)—N-ethyl-N-methyl-3-[1-(dimethylamino)ethyl]phenyl carbamate (15.0 g, 60.0 mmol) in isopropyl alcohol (75 mL). The resulting mixture was heated to 75-80° C. and then cooled to 20-25° C. The resulting suspension was filtered and washed with isopropanol and the solid was dried under vacuum at 40-50° C. to give crystalline (S)—N-Ethyl-N-methyl-3-[1-(dimethylamino)ethyl]-phenyl carbamate (2R,3R)-hydrogen tartrate (Rivastigmine hydrogen tartrate) $^1$H NMR (CDCl$_3$) δ 8.50-7.50 (s, 4H); 7.41 (t, J=7.8 Hz 1H); 7.30-7.16 (m, 3H); 4.44 (s, 2H); 4.34 (q, J=6.5 Hz, 1H); 3.50-3.34 (m, 2H); 3.02 (ad, 3H); 2.66 (s, 6H); 1.70 (d, J=6.8 Hz); 1.26-1.15 (m, 3H). PXRD (FIG. 1).

EXAMPLE 7

Preparation of (S)—N-Ethyl-N-methyl-3-[1-(dimethylamino)ethyl]-phenyl carbamate (2R,3R)-hydrogen tartrate from (S)-3-[1-Dimethylamino)ethyl] phenol and 1-[(N-ethyl-methylamino)carbonyl]-3-methyl-1H-imidazolium methyl sulfate Triethylamine (3.6 g, 35.4 mmol) and 1-{([N-ethyl-(N-methyl)amino]carbonyl}-3-methyl-1H-imidazolium methyl sulfate (9.1 g, 32.6 mmol) were added slowly to the cooled solution of (S)-3-[1-(dimethylamino)ethyl]phenol (4.5 g, 27.23 mmol) in acetonitirile (25 mL). The reaction mixture was stirred at 75-80° C. until reaction completion as determined by $^1$H NMR. The reaction mixture was evaporated and the obtained residue was diluted with water (30 mL) and toluene (30 mL) and then basified with 50% aq. NaOH solution at internal temperature below 10° C. The phases were separated and the aqueous phase was extracted with toluene. The combined organic phases were washed with water. The organic solution was evaporated under vacuum to give (S)—N-ethyl-N-methyl-3-[1-(dimethylamino)ethyl]phenyl carbamate. The residue dissolved in isopropanol (45 mL) and to the solution was added (2R,3R)-tartaric acid (4.08 g, 27.23 mmol) and heated to 70-80° C. The solution was cooled and the resulting suspension was filtered and dried to give (S)—N-Ethyl-N-methyl-3-[1-(dimethylamino)ethyl]-phenyl carbamate (2R,3R)-hydrogen tartrate (8.54 g, 78% yield). The $^1$H NMR spectrum of the product was identical to that of example 6.

EXAMPLE 8

Preparation of amorphous form of (S)—N-Ethyl-N-methyl-3-[1-(dimethylamino)ethyl]phenyl carbamate hydrogen-(2R,3R)-tartrate The solution of (S)—N-Ethyl-N-methyl-3-[1-(dimethylamino)ethyl]-phenyl carbamate hydrogen-(2R,3R)-tartrate (Rivastigmine hydrogen tartrate) (2 g) in water (4 mL) was stirred at 20-25° C. for 0.5-1 hour. The mixture was evaporated at 45-60° C. under vacuum to give a white solid. The obtained material was further dried at 40-45° C. for 10-12 hours under vacuum to obtain amorphous Rivastigmine hydrogen tartrate. PXRD (FIG. 2) and IR (FIG. 3).

As many changes can be made to the invention without departing from the scope of the invention, it is intended that all material contained herein be interpreted as illustrative of the invention and not in a limiting sense.

The invention claimed is:

1. A process for the preparation of an aminoalkyl phenyl carbamate compound of formula 1,

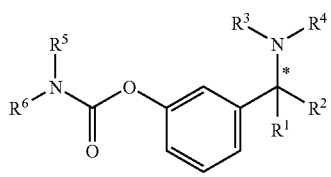

wherein $R^1$ and $R^2$ independently are hydrogen or $C_{1-6}$ alkyl; $R^3$ and $R^4$ are the same or different and each is a lower alkyl; or $R^3$ and $R^4$ together with the nitrogen to which they are attached form a cyclic moiety of a three to eight-member ring, with or without a hetero atom; $R^5$ and $R^6$ independently are hydrogen, linear, branched or cyclic $C_{1-6}$ alkyl, allyl, propargyl or benzyl; or $R^5$ and $R^6$ together with the nitrogen to which they are attached form a cyclic moiety of three to eight member ring, with or without a hetero atom; the carbon center marked with "*" is racemic or enantiomerically enriched (R)- or (S)-configuration; and pharmaceutically acceptable addition salts thereof comprising:

i) converting an amine $R^5R^6NH$ to a carbamoylimidazolium salt of formula 3

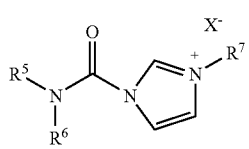

wherein $R^5$ and $R^6$ are as defined above; $X^-$ is a counterion and $R^7$ is an alkyl or aryl group;

ii) reacting in a solvent at a controlled reaction temperature the compound of formula 3 with a compound of formula 4,

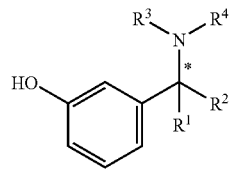

wherein $R^1$, $R^2$, $R^3$, $R^4$ and "*" are as defined above to give the compound of formula 1; and iii) isolating the compound of formula 1.

2. The process according to claim 1 wherein the reaction temperature for the step ii) ranges from −10° C. to 150° C.

3. The process according to claim 1 wherein the reaction temperature for the step ii) ranges from 20° C. to 100° C.

4. The process according to claim 1, 2 or 3 wherein $X^-$ is selected from the group consisting of $I^-$, $Br^-$, $Cl^-$, $F^-$, $(MeO)SO_3^-$, $SO_4^{2-}$, $BF_4^-$ and $OTf^-$.

5. The process according to claim 4 wherein $X^-$ is selected from the group consisting of $I^-$, $Br^-$, $(MeO)SO_3^-$, and $Otf^-$.

6. The process according to claim 1, 2 or 3 wherein $R^7$ is a $C_{1-7}$ alkyl or aryl group.

7. The process according to claim 6 wherein $R^7$ is a methyl or an ethyl group.

8. The process according to claim 1, 2 or 3 wherein the compound of formula 3 is prepared by a process comprising: a) reacting an amine $R^5R^6NH$ with N,N'-carbonyldiimidazole to form an intermediate compound wherein $R^5$ and $R^6$ independently are hydrogen, linear, branched or cyclic $C_{1-6}$ alkyl, allyl, propargyl or benzyl; or $R^5$ and $R^6$ together with the nitrogen to which they are attached form a cyclic moiety of three to eight member ring, with or without a hetero atom; and b) reacting the intermediate compound from step a) with $R^7X$ wherein $R^7$ is an alkyl or aryl group and X is selected from the group consisting of I, Br, Cl, F, $(MeO)SO_3$, $SO_4$, $BF_4$ and OTf.

9. The process according to claim 1, 2 or 3 wherein the solvent for the step ii) is selected from chlorinated hydrocarbons; alkyl and aryl nitriles; alkyl carboxylic acid esters; cyclic or acyclic ethers; alkyl cyclic and acyclic amides; cyclic or acyclic alkyl sulfoxides and sulfones; and aromatics.

10. The process according to claim 9 wherein the solvent for the step ii) is selected from the group consisting of dichloromethane, acetonitrile, tetrahydrofuran, ethyl acetate, methyl acetate and toluene.

11. A process for the preparation of racemic and enantiomerically enriched forms of ethylmethylcarbamic acid 3-[1-(dimethylamino)ethyl]phenyl ester of formula 6

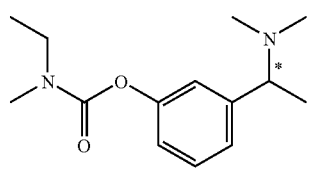

wherein the carbon centre designated "*" is racemic or enantiomerically enriched in the (R)- or (S)- configuration, comprising:

i) converting an amine N-ethyl-N-methylamine to carbamoylimidazolium salt of formula 7

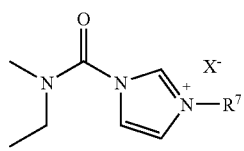

wherein X⁻ is a counterion and R⁷ is an alkyl or aryl group;
ii) reacting in a solvent at a controlled reaction temperature the compound of formula 7 with a compound of formula 8,

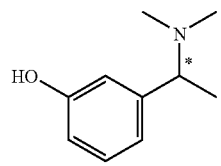

wherein the carbon centre designated "*" is as defined above, to give the compound of formula 6; and
iii) isolating the compound of formula 6.

12. The process according to claim 11 wherein the reaction temperature for the step ii) ranges from −10° C. to 150° C.

13. The process according to claim 11 wherein the reaction temperature for the step ii) ranges from 20° C. to 100° C.

14. The process according to claim 11, 12 or 13 wherein X⁻ is selected from the group consisting of I⁻, Br⁻, Cl⁻, F⁻, (MeO)SO₃⁻, SO₄²⁻, BF₄⁻ and Otf⁻.

15. The process according to claim 14 wherein X⁻ is I⁻ or Otf⁻.

16. The process according to claim 11, 12 or 13 wherein R⁷ is a C₁₋₇ alkyl or aryl group.

17. The process according to claim 16 wherein R⁷ is a methyl or an ethyl group.

18. The process according to claim 11, 12 or 13 wherein the compound 7 is prepared by a process comprising: a) reacting an amine N-ethyl-N-methylamine with N,N'-carbonyldiimidazole to form an intermediate compound, and b) reacting the intermediate compound from step a) with R⁷X, wherein R⁷ is a C₁₋₇ alkyl or aryl group and X is selected from the group consisting of I⁻, Br⁻, Cl⁻, F⁻, (MeO)SO₃⁻, SO₄²⁻, BF₄⁻ and OTf⁻.

19. The process according to claim 11, 12 or 13 wherein the solvent for the step ii) is selected from chlorinated hydrocarbons; alkyl and aryl nitriles; alkyl carboxylic acid esters; cyclic or acyclic ethers; alkyl cyclic and acyclic amides; cyclic or acyclic alkyl sulfoxides and sulfones; and aromatics.

20. The process according to claim 19 wherein the solvent for the step ii) is selected from the group consisting of dichloromethane, acetonitrile, tetrahydrofuran, ethyl acetate, methyl acetate and toluene.

21. The process according to claim 11, 12 or 13 wherein the compound of formula 6 is (S)-N-ethyl-N-methyl-3-[1-(dimethylamino)ethyl]phenyl carbamate-(2R,3R)-Hydrogen-tartrate salt.

22. The process according to claim 11, 12 or 13 wherein the compound of formula 6 is the crystalline form of (S)-N-ethyl-N-methyl-3-[1-(dimethylamino)ethyl]phenyl carbamate-(2R,3R) hydrogen-tartrate salt.

23. The process according to claim 11, 12 or 13 wherein the compound of formula 6 is the amorphous form of (S)-N-ethyl-N-methyl-3-[1-(dimethylamino)ethyl]phenyl carbamate-(2R, 3R) hydrogen-tartrate salt.

24. A process for the preparation of an amorphous form of (S)-N-ethyl-N-methyl-3-[1-(dimethylamino)ethyl]phenyl carbamate-(2R,3R) hydrogen-tartrate salt comprising stirring a solution of (S)-N-ethyl-N-methyl-3-[1-(dimethylamino)ethyl]phenyl carbamate-(2R,3R) hydrogen-tartrate in water for 0.5-1 hour at 20-25° C., evaporating the water at 45-60° C. under vacuum to give a white solid, and drying the white solid at 40-45° C. for 10-12 hours under vacuum.

25. The amorphous form of (S)-N-ethyl-N-methyl-3-[1-(dimethylamino)ethyl]phenyl carbamate-(2R,3R) hydrogen-tartrate salt.

26. The compound of formula 7 wherein X⁻ is a counterion selected from the group consisting of I⁻, Br⁻, Cl⁻, F⁻, (MeO)SO₃⁻, SO₄²⁻, BF₄⁻ and OTf⁻; and R⁷ is a C₁₋₇ alkyl or aryl group.

27. N-ethyl-N-methyl-1H-imidazole-1-carboxamide.

28. 1-{[N-ethyl-(N-methyl)amino]carbonyl}-3-methyl-1H-imidazolium iodide.

29. 1-{[N-ethyl-(N-methyl)amino]carbonyl}-3-methyl-1H-imidazolium methyl sulfate.

30. A process for the preparation of an aminoalkyl phenyl carbamate compound of formula 1,

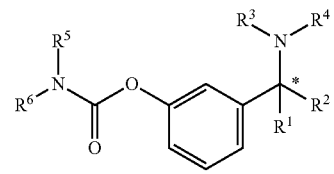

wherein R¹ and R² independently are hydrogen or C₁₋₆ alkyl; R³ and R⁴ are the same or different and each is a lower alkyl; or R³ and R⁴ together with the nitrogen to which they are attached form a cyclic moiety of a three to eight-member ring, with or without a hetero atom selected from the group consisting of: nitrogen and oxygen; R⁵ and R⁶ independently are hydrogen, linear, branched or cyclic C₁₋₆ alkyl, allyl, propargyl or benzyl; or R⁵ and R⁶ together with the nitrogen to which they are attached form a cyclic moiety of three to eight member ring, with or without a hetero atom selected from the group consisting of: nitrogen and oxygen; the carbon center marked with "*" is racemic or enantiomerically enriched (R)- or (S)- configuration; and pharmaceutically acceptable addition salts thereof comprising:

i) converting an amine R⁵R⁶NH to a carbamoylimidazolium salt of formula 3

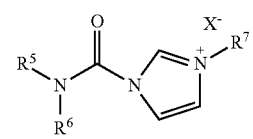

wherein R⁵ and R⁶ are as defined above; X⁻ is a counterion and R⁷ is an alkyl or aryl group;

ii) reacting in a solvent at a controlled reaction temperature of from 20° C. to 100° C. the compound of formula 3 with a compound of formula 4,

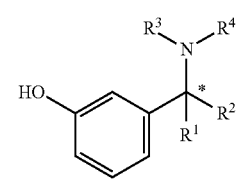

wherein R¹, R², R³, R⁴ and "*" are as defined above to give the compound of formula 1; and iii) isolating the compound of formula 1.

31. The process according to claim 30 wherein the compound of formula 3 is prepared by a process comprising: a) reacting an amine $R^5R^6NH$ with N,N'-carbonyldiimidazole to form an intermediate compound wherein $R^5$ and $R^6$ independently are hydrogen, linear, branched or cyclic $C_{1-6}$ alkyl, allyl, propargyl or benzyl; or $R^5$ and $R^6$ together with the nitrogen to which they are attached form a cyclic moiety of three to eight member ring, with or without a hetero atom selected from the group consisting of: nitrogen and oxygen; and b) reacting the intermediate compound from step a) with $R^7X$ wherein $R^7$ is an alkyl or aryl group and X is selected from the group consisting of I, Br, Cl, F, $(MeO)SO_3$, $SO_4$, $BF_4$ and OTf.

32. The process according to claim 31 wherein the solvent for the step ii) is selected from dichloromethane, dichloroethane, chlorobenzene, acetonitrile, ethyl acetate, methyl acetate, 1,2-dimethoxyethane, dimethoxymethane, tetrahydrofuran, 1,4-dioxane, N,N-dimethylformamide, N,N-dimethylacetamide, 1-methyl-2-pyrrolidinone, dimethylsulfoxide, tetramethylene sulfone, toluene, and xylenes.

33. The process according to claim 31 wherein the solvent for the step ii) is selected from the group consisting of dichloromethane, acetonitrile, tetrahydrofuran, ethyl acetate, methyl acetate and toluene.

34. A process for the preparation of racemic and enantiomerically enriched forms of ethylmethylcarbamic acid 3-[1-(dimethylamino)ethyl]phenyl ester of formula 6

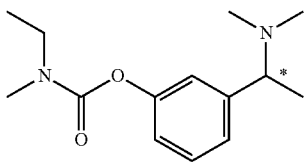

6 wherein the carbon centre designated "*" is racemic or enantiomerically enriched in the (R)- or (S)- configuration, comprising:

i) converting an amine N-ethyl-N-methylamine to carbamoylimidazolium salt of formula 7

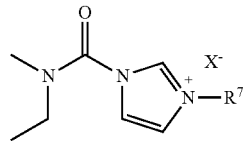

7 wherein $X^-$ is a counterion and $R^7$ is an alkyl or aryl group;

ii) reacting in a solvent at a controlled reaction temperature of from 20° C. to 100° C. the compound of formula 7 with a compound of formula 8,

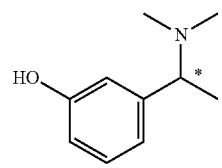

8 wherein the carbon centre designated "*" is as defined above, to give the compound of formula 6; and iii) isolating the compound of formula 6.

35. The process according to claim 34 wherein the solvent for the step ii) is selected from dichloromethane, dichloroethane, chlorobenzene, acetonitrile, ethyl acetate, methyl acetate, 1,2-dimethoxyethane, dimethoxymethane, tetrahydrofuran, 1,4-dioxane, N,N-dimethylformamide, N,N-dimethylacetamide, 1-methyl-2-pyrrolidinone, dimethylsulfoxide, tetramethylene sulfone, toluene, and xylenes.

36. The process according to claim 34 wherein the solvent for the step ii) is selected from the group consisting of dichloromethane, acetonitrile, tetrahydrofuran, ethyl acetate, methyl acetate and toluene.

* * * * *